United States Patent [19]

Ganter et al.

[11] Patent Number: 5,635,206
[45] Date of Patent: Jun. 3, 1997

[54] PROCESS FOR LIPOSOMES OR PROLIPOSOMES

[75] Inventors: Sabina Ganter, Lörrach-Stetten; Karl M. Völker, Freiburg, both of Germany

[73] Assignee: Hoffmann-La Roche Inc., Nutley, N.J.

[21] Appl. No.: 350,306

[22] Filed: Dec. 6, 1994

[30] Foreign Application Priority Data

Jan. 20, 1994 [CH] Switzerland .................. 174/94

[51] Int. Cl.$^6$ .................................. A61K 9/127
[52] U.S. Cl. .......................... 424/450; 264/4.1
[58] Field of Search ............. 424/450; 514/78; 264/4.1, 4.3

[56] References Cited

U.S. PATENT DOCUMENTS

| | | | |
|---|---|---|---|
| 4,693,999 | 9/1987 | Axelsson | 514/174 |
| 4,998,678 | 3/1991 | Durr | 241/171 |
| 5,141,674 | 8/1992 | Leigh | 252/305 |
| 5,310,734 | 5/1994 | Losch et al. | 514/78 |

FOREIGN PATENT DOCUMENTS

| | | |
|---|---|---|
| 499299 | 8/1992 | European Pat. Off. . |
| 521398 | 1/1993 | European Pat. Off. . |
| 87/07502 | 12/1987 | WIPO . |
| 94/28876 | 12/1994 | WIPO . |

OTHER PUBLICATIONS

Gerhartz, W., Ullmann's Encyclopedia of Industrial Chemistry, 5th Edition, vol. B2, pp. 5–20 to 5–21 and 5–36 to 5–38 (1988).

*Primary Examiner*—Gollamudi S. Kishore
*Attorney, Agent, or Firm*—George W. Johnston; William H. Epstein; John P. Parise

[57] ABSTRACT

The invention relates to a process for the preparation of liposomes or proliposomes in which a mixture suitable for their preparation is milled in an agitator-ball mill.

12 Claims, No Drawings

1

PROCESS FOR LIPOSOMES OR PROLIPOSOMES

BRIEF SUMMARY OF THE INVENTION

The invention relates to a process for the preparation of liposomes or proliposomes in which a mixture suitable for their preparation is milled in an agitator-ball mill.

DETAILED DESCRIPTION OF THE INVENTION

The invention relates to a process for the preparation of liposomes or proliposomes in which a mixture suitable for their preparation is milled in an agitator-ball mill.

Due to the ability of liposomes to penetrate into the skin, they can be used, inter alia, in cosmetics or in dermal therapy. They may be loaded with moisture or otherwise with a wide variety of active ingredients or substances, inter alia, vitamins. Due to the amphiphilic properties of liposomes, the active ingredients or substances are transported deep into the skin and thus the delivery of such active ingredients or substances to the desired site is guaranteed.

Various methods for the preparation of liposomes and proliposomes are known. However, most of these methods are suitable only on a laboratory scale, for example, the film method. Such methods are known to a person skilled in the art and are described, for example, in *Liposome Technology*; Gregoriadis G., (ed.), Vol. I–III (1993). Rotor-stator homogenization or liquid high-pressure homogenization are suitable, for example, for the preparation of liposomes on a larger scale. Although liquid high-pressure homogenizers, which include, for example, liquid jet high-pressure homogenizers (microfluidizers) or liquid slot nozzle high-pressure homogenizers, are very well suited for the preparation of liposomes, they have the disadvantage that only liquid materials can be processed with them. They are unsuitable for very concentrated and viscous formulations. In addition, the reproducibility of the particle size is, especially when liposomes are prepared using liquid slot nozzle high-pressure homogenizers, not always satisfactory. Another disadvantage of the aforementioned methods is the fact that high energies act on the particles.

Accordingly, there is a need for a process for the preparation of liposomes and proliposomes which can be operated under mild conditions and without great dilution. The process should permit the preparation, under mild conditions, of liposomes or proliposomes having a regular structure in which one or more active substances, which may be added, are uniformly dispersed. In addition, the process should be readily operable on an industrial scale.

It has now been found that liposomes and/or proliposomes can be prepared under mild conditions by milling a mixture which is suitable for the preparation of liposomes and/or proliposomes in an agitator ball-mill.

An agitator-ball mill is a particular type of ball mill. The homogenization and size reduction in this mill is brought about by forces transferred by the agitator to the freely movable balls, preferably composed of glass, and from there to the material being milled.

The process according to the invention is very mild and can also be applied on an industrial scale. It is equally suitable for the preparation of proliposomes, for the manufacture of liposomes from proliposomes and for the direct preparation of liposomes. The size and lamellarity of the proliposomes and the size of the liposomes can be varied as required by the choice of homogenization conditions (for example, rotor circumferential speed, milling time, ball size, filling level, temperature).

It is possible to prepare, by the process according to the invention, proliposomes or liposomes which are either unloaded or otherwise loaded with one or more lipophilic and/or hydrophilic substances.

Lecithins of various origin, for example, egg lecithin or soya lecithin are used in mixtures which can be used to prepare liposomes or proliposomes; such lecithins are commercially available.

Solubilizers which can be used are polar organic solvents, for example, alcohols, such as, ethanol, iso-propanol and the like.

Suitable compounds which can be incorporated are lipophilic or hydrophilic substances, such as, lipophilic or hydrophilic vitamins, pharmaceuticals, as well as, flavorants and odorants. Examples of these are the fat-soluble vitamins and vitamin derivatives (A, K and E), their precursors (b-carotene), carotenoids or fat-soluble pharmaceuticals, such as, diazepam, amphotericin B, econazole, corticoids and the like. Examples of suitable hydrophilic compounds are the water-soluble vitamins (B complex or vitamin C) or hydrophilic pharmaceuticals, such as, heparin, cisplatin and the like. Examples of fat-soluble flavorants and odorants are citrus oils, peppermint oil and the like. Examples of hydrophilic flavorants and odorants which can be incorporated are vanilla extract, cocoa flavor or tobacco flavors.

The added lipophilic or hydrophilic compounds are incorporated into the liposomes or proliposomes by the process according to the invention under very mild conditions. Very thorough mixing and thus homogeneous dispersion of the added compounds in the bilayer is ensured.

For the preparation of proliposomes, it is possible in the process according to the invention, in contrast to conventional methods, to use very concentrated and viscous lecithin mixtures.

A mixture suitable for the preparation of proliposomes using an agitator-ball mill contains

| | |
|---|---|
| 50–90% | lecithin |
| 15–50% | solubilizer |
| 0–10% | water |
| 0–20% | hydrophilic and/or lipophilic compounds to be incorporated. |

The preparation of proliposomes by the process according to the invention is typically carried out by milling a mixture which has been prepared according to the aforementioned formula in an agitator-ball mill. In this connection, it is possible, depending on the required structure, to charge between 50 and 90% of the volume of the agitator-ball mill with commercially available beads having a diameter of 0.2 to 6 mm, preferably glass beads of a diameter of 0.3 to 1.5 mm. The structure of the product can be influenced by the milling speed, the milling time and the temperature. The rotor circumferential speed is preferably 5–15 m/s (meters/seconds).

Proliposomal formulations preparations by the process of the invention are distinguished by a very regular, long lamellar structure. They contain very high lecithin concentrations, and active substances, which may be added, are homogeneously dispersed.

The proliposomes prepared by the process according to the invention can be stored very easily because of their high concentration and their relatively high content of alcohol.

The proliposomes described above can be converted after the addition of water in a known manner, such as, for example, by homogenization with a liquid jet high-pressure homogenizer, into liposomes. It is remarkable, in this connection, that the liposomes from proliposomal compositions prepared according to the invention are, as a rule, smaller than liposomes which are manufactured directly.

The liposomes can be prepared from the proliposomes described above, after addition of water, also according to the invention by milling the proliposomal composition in an agitator-ball mill. For this purpose, the proliposomal composition is typically mixed with water until the water content is between 35% and 95% and then milled in the agitator-ball mill.

As already mentioned, it is also possible according to the invention to prepare liposomes directly by milling suitable mixtures in the agitator-ball mill. A mixture suitable for the preparation of liposomes using an agitator-ball mill contains

| | |
|---|---|
| 1–30% | lecithin |
| 1–15% | solubilizer |
| 35–95% | water |
| 0–5% | hydrophilic and/or lipophilic compounds to be incorporated. |

In this case, between 50% and 90% of the volume of the agitator-ball mill is charged with commercially available beads having a diameter of 0.2 to 6 mm, preferably from 0.3 to 1.5 mm. The structure of the product can also be influenced, in this case, by the milling speed and the milling time. The rotor circumferential speed is 5–15 m/s. It is possible, in this way, to prepare specifically large and very homogeneous liposomes (1–5 µm).

The following Examples further illustrate the invention. All temperatures are given in degrees centigrade.

EXAMPLE 1

Preparation of a proliposomal solution

| Formula: | 120 g of lecithin (= 60% wt./wt.) |
|---|---|
| | 24 g of tocopherol acetate (= 12% wt./wt.) |
| | 42 g of ethanol (= 21% wt./wt.) |
| | ad 200 g of distilled water (= 7% wt./wt.) |

A mixture of lecithin, ethanol and dl-α-tocopherol was milled in an agitator-ball mill at a rotor circumferential speed of 15 m/s, while cooling for 20 minutes. Glass beads of diameter 1 mm were used for this purpose. Very long lamellar structures resulted. The formulation had a high viscosity but was still capable of flowing.

EXAMPLE 2

Preparation of liposomes

| Formula: | 20 g of soya lecithin (= 10% wt./wt.) |
|---|---|
| | 7 g of ethanol (= 3.5% wt./wt.) |
| | 2 g of tocopherol acetate (= 1% wt./wt.) |
| | ad 200 g of distilled water (= 85.5% wt./wt.) |

The mixture is initially hydrated for 5 minutes and subsequently milled in the agitator-ball mill at a rotor circumferential speed of 10 m/s, while cooling for 20 minutes. Glass beads of diameter 0.3 mm were used for this. The resulting liposomes had a diameter of 1–2 µm.

EXAMPLE 3

Preparation of liposomes

| Formula: | 20 g of soya lecithin (= 10% wt./wt.) |
|---|---|
| | 7 g of ethanol (= 3.5% wt./wt.) |
| | 8 g of tocopherol acetate (= 4% wt./wt.) |
| | ad 200 g of distilled water (= 82.5% wt./wt.) |

The mixture was initially hydrated for 5 minutes and subsequently milled in the agitator-ball mill at a rotor circumferential speed of 10 m/s, while cooling for 60 minutes. Glass beads of diameter 0.3 mm were used. The resulting multilamellar liposomes had a size of 2–5 µm.

EXAMPLE 4

Preparation of liposomes from proliposomes

| Formula: | 31 g of proliposomes from Example 1 (60% lecithin, 12% tocopherol acetate, 21% ethanol, 7% distilled water) |
|---|---|
| | ad 200 g of distilled water. |

The mixture was initially stirred on a magnetic stirrer for 5 minutes and subsequently milled in the agitator-ball mill with 0.5 mm glass beads at a rotor circumferential speed of 10 m/s for 15 minutes. The resulting unilamellar liposomes had a diameter of 50–100 nm and the following final composition:

| | |
|---|---|
| 18.6 g of soya lecithin (= 9.3% wt./w)t. |
| 6.51 g of ethanol (= 3.26% wt./wt.) |
| 3.72 g of tocopherol acetate (= 1.86% wt./wt.) |
| 171.17 g of distilled water (= 85.6% wt./wt.) |

We claim:

1. A process for preparing proliposomes, which comprises milling in an agitator-ball mill a mixture comprising 50 to 90% by weight of lecithin, 15 to 50% by weight of a solubilizer, 0 to 10% by weight of water, and 0 to 20% by weight of a compound to be incorporated, the milling being conducted at a milling speed and for a milling time effective to prepare proliposomes.

2. A process according to claim 1, wherein the milling is in an agitator-ball mill at a circumferential speed of 5 to 15 meters/second.

3. A process according to claim 1, wherein the agitator-ball mill is charged with glass beads having a diameter of 0.2 to 6 mm.

4. A process according to claim 3, wherein the agitator-ball mill is charged with glass beads having a diameter of 0.3 to 1.5 mm.

5. A process for preparing liposomes, which comprises milling in an agitator-ball mill a mixture comprising 1 to 30% by weight of lecithin, 1 to 15% by weight of a solubilizer, 35 to 95% by weight of water, and 0 to 5% by weight of a compound to be incorporated, the milling being conducted at a milling speed and for a milling time effective to prepare liposomes.

6. A process according to claim 5, wherein the milling is in an agitator-ball mill at a circumferential speed of 5 to 15 meters/second.

7. A process according to claim 5, wherein the agitator-ball mill is charged with glass beads having a diameter of 0.2 to 6 mm.

8. A process according to claim 7, wherein the agitator-ball mill is charged with glass beads having a diameter of 0.3 to 1.5 mm.

9. A process for preparing liposomes, which comprises:
(a) milling in an agitator-ball mill a mixture comprising 50 to 90% by weight of lecithin, 15 to 50% by weight of a solubilizer, 0 to 10% by weight of water, and 0 to 20% by weight of a compound to be incorporated, the milling being conducted at a milling speed and for a milling time effective to prepare proliposomes in a milled mixture;
(b) adding water to the milled mixture until the water content is between 35% and 95% by weight of the milled mixture to form a dilute mixture; and
(c) milling in an agitator-ball mill the dilute mixture, the milling being conducted at a milling speed and for a milling time effective to prepare liposomes.

10. A process according to claim 9, wherein the milling is in an agitator-ball mill at a circumferential speed of 5 to 15 meters/second.

11. A process according to claim 9, wherein the agitator-ball mill is charged with glass beads having a diameter of 0.2 to 6 mm.

12. A process according to claim 11, wherein the agitator-ball mill is charged with glass beads having a diameter of 0.3 to 1.5 mm.

* * * * *